(12) United States Patent
Weidinger et al.

(10) Patent No.: US 12,186,122 B2
(45) Date of Patent: Jan. 7, 2025

(54) AUTOMATIC REGULATION OF A POSITION OF AN X-RAY FOCUS OF AN X-RAY IMAGING SYSTEM

(71) Applicant: Siemens Healthineers AG, Forchheim (DE)

(72) Inventors: Thomas Weidinger, Erlangen (DE); Ulf Lanz, Erlangen (DE); Johannes Gareus, Forchheim (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 392 days.

(21) Appl. No.: 17/726,803

(22) Filed: Apr. 22, 2022

(65) Prior Publication Data

US 2022/0338832 A1  Oct. 27, 2022

(30) Foreign Application Priority Data

Apr. 27, 2021  (EP) .................... 21170605

(51) Int. Cl.
*A61B 6/08* (2006.01)
*A61B 6/00* (2006.01)
*A61B 6/03* (2006.01)

(52) U.S. Cl.
CPC ............... *A61B 6/547* (2013.01); *A61B 6/08* (2013.01); *A61B 6/032* (2013.01)

(58) Field of Classification Search
CPC ........... A61B 6/547; A61B 6/08; A61B 6/032
See application file for complete search history.

(56) References Cited

U.S. PATENT DOCUMENTS

| 2004/0190682 A1 | 9/2004 | Deuringer et al. |
| 2005/0094762 A1 | 5/2005 | Dunham et al. |
| 2008/0080664 A1 | 4/2008 | Bernhardt et al. |
| 2018/0261420 A1 | 9/2018 | Holch et al. |

FOREIGN PATENT DOCUMENTS

| DE | 10301071 A1 | 7/2004 | |
| DE | 102006046734 A1 | 4/2008 | |
| DE | 102017203932 A1 | 9/2018 | |
| EP | 3528274 A1 | 8/2019 | |
| WO | WO-2011105472 A1 * | 9/2011 | ............. A61B 6/032 |

* cited by examiner

*Primary Examiner* — David P Porta
*Assistant Examiner* — Fani Polyzos Boosalis
(74) *Attorney, Agent, or Firm* — Harness, Dickey & Pierce, P.L.C.

(57) ABSTRACT

In a method for regulating a position of an X-ray focus on the anode of an X-ray source of a scan unit of an X-ray imaging system, a combined actual position of the X-ray focus is determined by a combination of a measured position of the X-ray focus and a model-based position of the X-ray focus, which is determined based on a measured value of a deflection current. On the basis of the combined actual position and a target position, a manipulated variable is determined. On the basis of the determined manipulated variable, a regulation is performed to correct a deviation of the position of the X-ray focus from the target position.

20 Claims, 9 Drawing Sheets

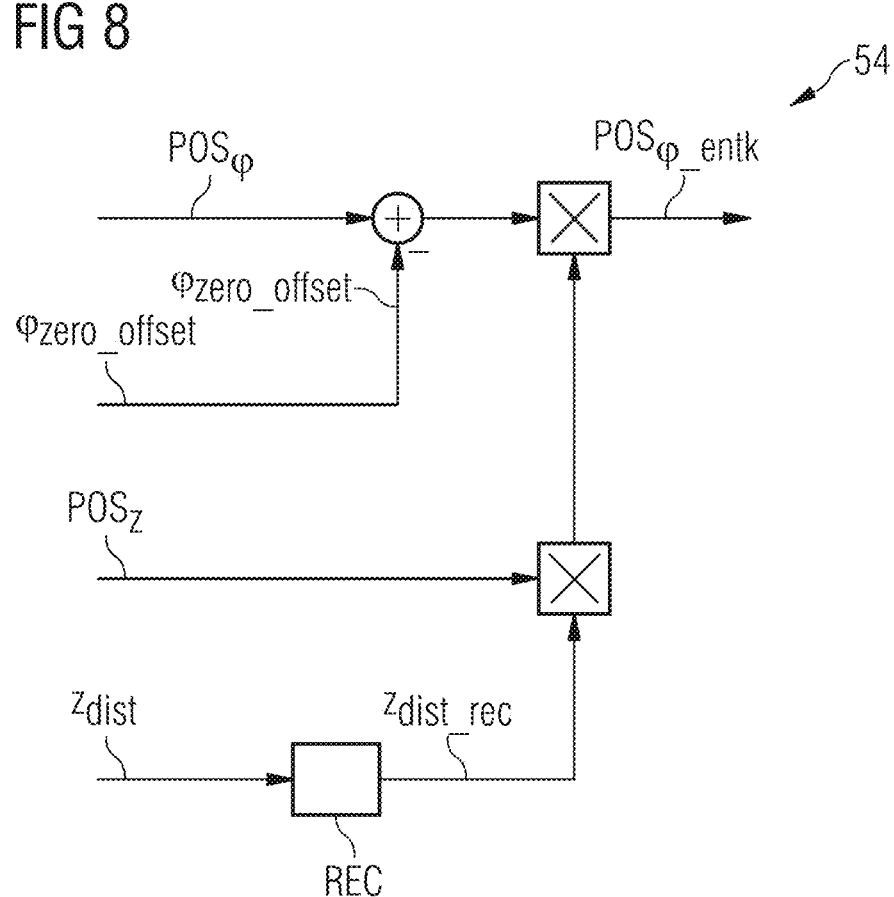

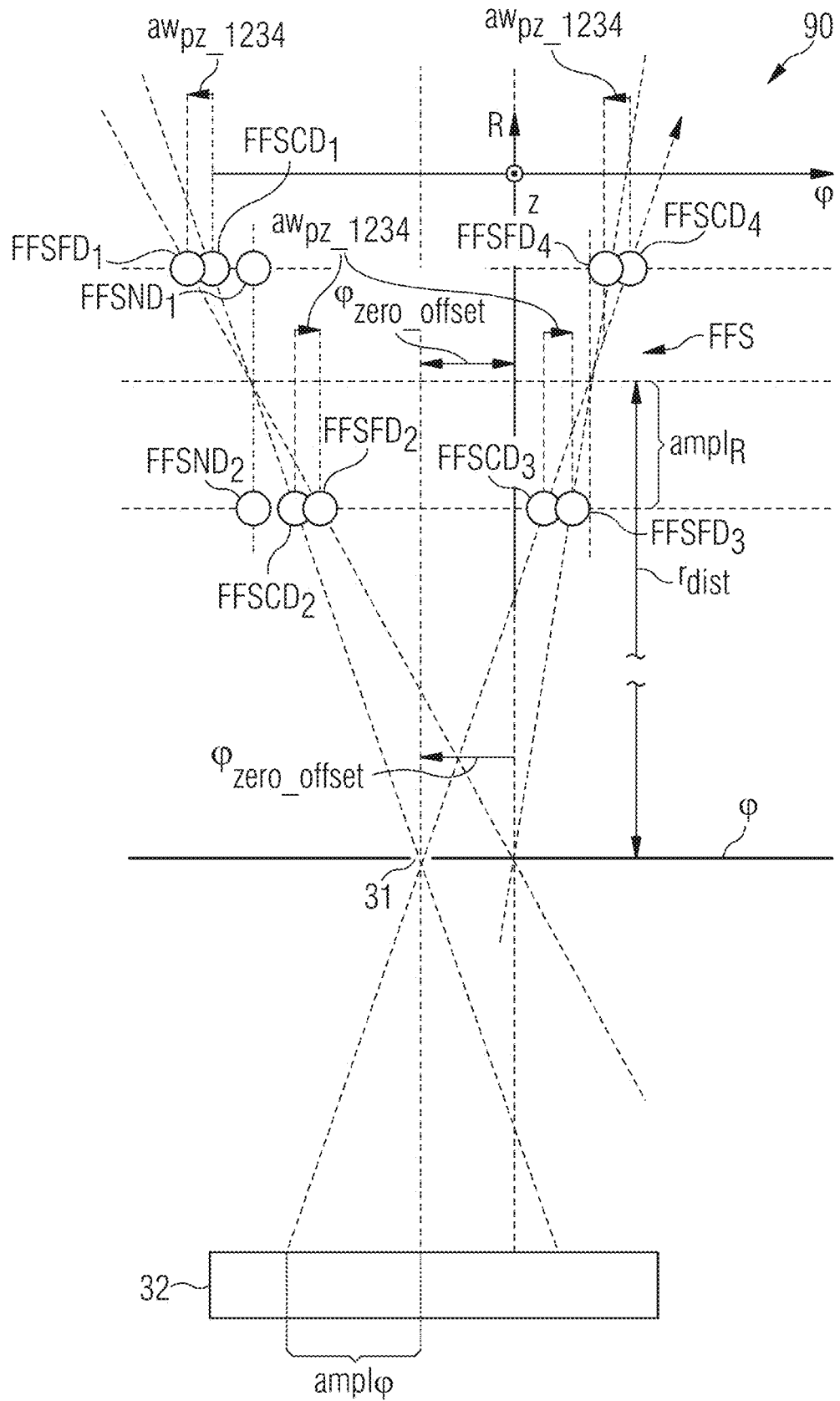

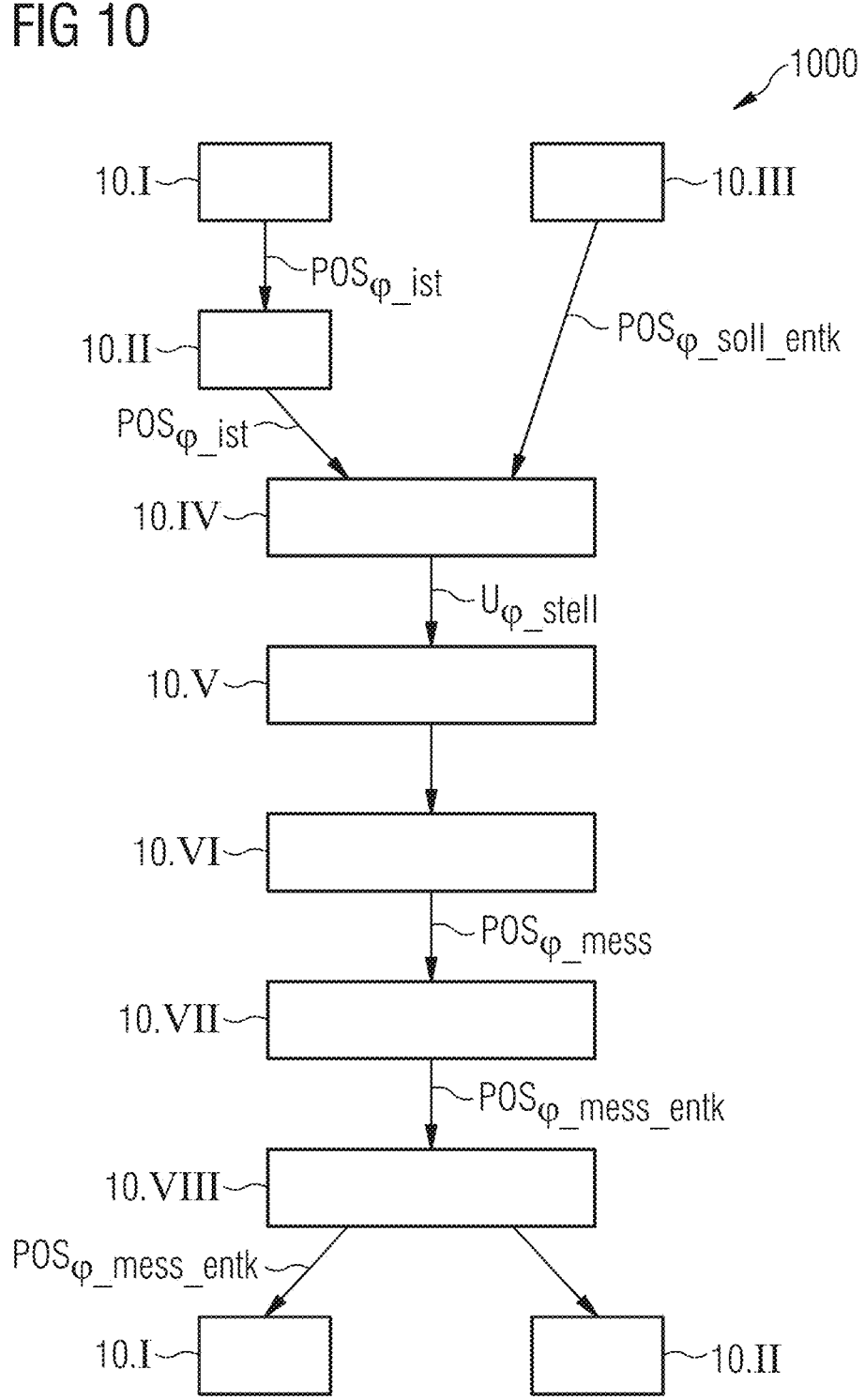

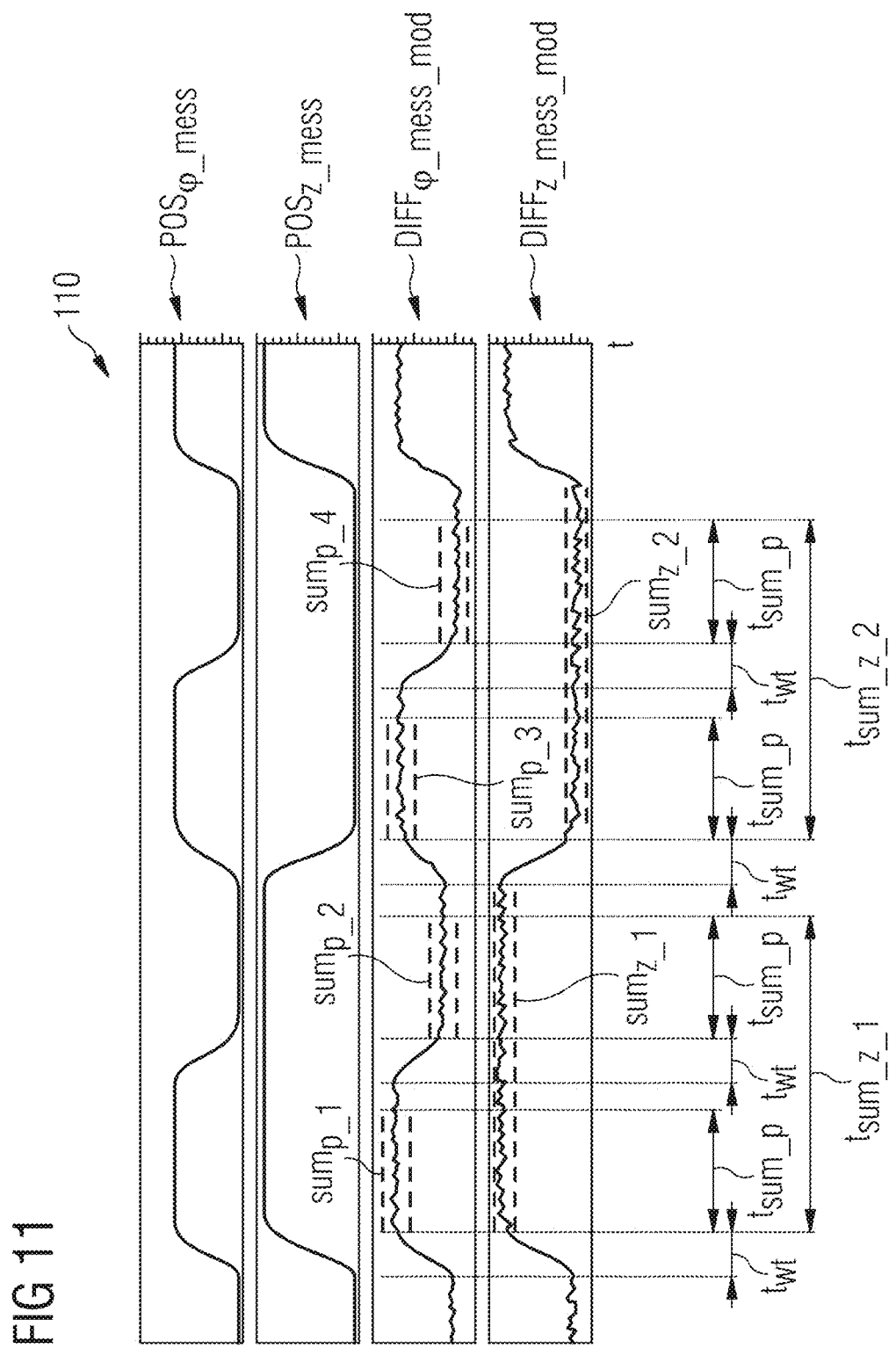

AUTOMATIC REGULATION OF A POSITION OF AN X-RAY FOCUS OF AN X-RAY IMAGING SYSTEM

CROSS-REFERENCE TO RELATED APPLICATION(S)

The present application claims priority under 35 U.S.C. § 119 to European Patent Application No. EP 21170605.6 filed Apr. 27, 2021, the entire contents of which are incorporated herein by reference.

FIELD

Embodiments of the present invention relate to a method for regulation of a position of an X-ray focus on an anode of an X-ray beam source of a scan unit of an X-ray imaging system. Further, embodiments of the present invention relate to a regulation device. Furthermore, embodiments of the present invention relate to an X-ray imaging system.

BACKGROUND

With the help of modern imaging methods, two- or three-dimensional image data are often generated that can be used to visualize a patient to be imaged, for example a person or an animal, and also for other applications.

A special type of medical imaging is implemented using computer tomography. In computer tomography systems, also called CT systems for short, three-dimensional slice images of the interior of an object to be examined are generated with the aid of a two-dimensional image detection process. For this purpose, individual images of the patient, a volume calculation (image) on the basis of which images is determined, are generated from different solid angles using an imaging system, which usually has an X-ray source rotating around the object to be examined and an X-ray detector rotating with it. The mentioned functional elements are supported rotatable about a system axis in a gantry housing, also referred to as a gantry frame, which is arranged in a ring around an examination object receiving space. Electrons are emitted from a cathode in the X-ray source and are accelerated to an anode, also referred as anode plate. On the anode plate, the electrons are focused on a so-called focal spot, also called X-ray focus, and they cause the emission of an X-ray beam. FIG. 1 shows a general schematic representation of a computer tomography system in order to clarify its general structure.

When the imaging system is rotated, a rotation angle φ is assigned to the imaging system. The direction of rotation in the detector plane is called the φ-direction. The direction perpendicular to this, which is oriented in the direction of the axis of rotation of the imaging system, is referred to as the z-direction, i.e. the direction that is parallel to the z-axis or system axis.

The maximum possible optical resolution with regard to the angle of rotation φ and the z-direction is limited by the physical resolution of the X-ray detector when the focal spot is in a fixed position on the anode plate of the X-ray source. In order to increase this resolution even further, the method of the jump focus, also known as "Flying Focal Spot" and abbreviated to "FFS", was developed. In this case, recordings are made in chronological order with different positions of the focal spot in the X-ray source, whereby the position of the focal spot on the anode is shifted by half a distance of the resolution in the φ-direction and in z-direction from the point of view of the detector. As a result, the resolution of the imaging in the φ-direction and in the z-direction can be doubled in each case. The shifting of the focal spot on the anode can also take place in more than two stages, so that the resolution can be increased even further in accordance with the number of stages. For this method, the focal spot position on the anode plate in the X-ray source must be changed dynamically from one recording to the next. The recording time of the individual recordings is sometimes in the range of several 100 µs, e.g. 250 µs. Due to the potential for improvement in imaging through shorter recording times, the recording time is being reduced further and further in the context of new developments, for example to a time of 100 µs. When the position of the X-ray beam changes on the X-ray detector, the image becomes blurred. The motion blur is smaller, the shorter the time of the change of position is compared to the total time of the recording in a jump position. By reducing the recording time for each jump position, it is necessary to shorten the time required to change the jump position in order not to increase the motion blur.

In addition, the following effects lead to motion blurring:
mechanical tolerances in the anode plate and
deflection effects of the electron beam due to stray fields of the anode drive.

In order to reduce such effects as well, the focal spot position or the position of the X-ray focus is usually detected by a position detection unit and regulated in a closed control loop.

The position of the X-ray focus on the anode is recorded via slits in the X-ray shield outside the main X-ray exit. The X-ray light hits position detection elements through the slits, which determine a position of the X-ray focus in the φ-direction and z-direction. Since the slits are located outside the main X-ray exit, a measured value is obtained for measuring the φ-position, which contains a coupling of the φ-position with the z-position, which is illustrated in FIG. 9. The position determined is therefore initially not the actual position of the X-ray focus on the anode and hence, the determined position has to be converted.

So far, a dynamic position of a jump focus has been achieved by a magnetic deflection of the X-ray focus in the φ-direction and in the z-direction and thus also a deflection of the X-ray beam in the φ-direction and in the z-direction. The position of the X-ray focus is regulated via a closed control loop. The control loop can conventionally be designed, for example, as a cascaded control loop with an inner current control loop and an outer position control loop. In this case, the dynamics of the control loop are essentially determined by the dynamics of the position detection and in particular by the dead time of the position detection and the transmission of the measured value of the position. The dead time of the position detection and the transmission of the measured value of the position cannot be reduced significantly due to the processing time of the analog and digital electronic signal processing. The dynamics of the position detection cannot be increased any further due to the necessary suppression of interference signals such as noise. Therefore, the dynamics can no longer be significantly increased in a cascaded control loop.

SUMMARY

The inventors have identified a problem of developing a regulation of a control of a position of a jump focus with improved dynamics.

This object is achieved by a method for regulating a position of an X-ray focus on the anode of an X-ray source of a scan unit of an X-ray imaging system according to patent claim 1, by a regulation device according to patent claim 10 and by an X-ray imaging system according to claim 12.

In the method, according to embodiments of the present invention, for regulating a position of an X-ray focus on the anode of an X-ray source of a scan unit of an X-ray imaging system, preferably a computer tomography system, a regulation of a deflection current of an X-ray focus in the X-ray beam source of the scan unit and a regulation of the position of the X-ray focus is performed via a common control unit and a common control system in a common control loop. The electron beam on the anode or the point of impact of the electron beam in the X-ray source on the anode plate should be referred to as the X-ray focus.

In the method, a combined actual position of the x-ray focus is determined by combining a measured position of the x-ray focus and a model-based position of the x-ray focus, which is determined on the basis of a measured value of a deflection current. On the basis of the combined actual position and a target position of the X-ray focus on the anode, a manipulated variable, preferably an electrical voltage, is determined to generate a deflection current for deflecting the electron beam from the X-ray source. On the basis of the determined manipulated variable, a regulation is carried out to correct any deviation of the position of the X-ray focus from the target position. For der determination of the measured position and the target position of the x-ray focus, single coordinate values, for example the φ-coordinate of the x-ray focus, also referred as φ-position, and the z-coordinate of the x-ray focus, also referred as z-position, can be determined and be used for the correction of the corresponding coordinate of the position of the x-ray focus.

In contrast to conventional regulation methods for regulating the position of a jump focus, according to embodiments of the present invention, no cascaded regulation, but a single-loop regulation of the position of the X-ray focus with a dynamic model-based calculation of the position on the basis of the measured current is carried out. In this way, the problem of the idle time that occurs during position detection can advantageously at least be reduced. As a result, a more dynamic control of the position of an X-ray focus and in particular a jump focus is achieved. This results in a significant improvement in the control dynamics and a reduction in the susceptibility to interference in the position control, in particular of a highly dynamic jump focus, and thus an improved image quality. The target position of the X-ray focus can be better regulated due to the higher control dynamics. The jump transitions from one position of the X-ray focus to the next position are shorter in time and the transition times have a significantly increased reproducibility.

The regulation device according to embodiments of the present invention comprises a control loop for regulating and controlling a position of an x-ray focus on the anode of an x-ray source of a scan unit of an x-ray imaging system, preferably a computer tomography system. The control loop includes a plant model unit for determining a combined actual position of the X-ray focus by combining a measured position of the X-ray focus and a model-based position of the X-ray focus, which is determined on the basis of a measured value of a deflection current. Part of the control loop is also a regulation unit for generating a manipulated variable, preferably an electric voltage for generating a deflection current of a magnet for controlling an electron beam for generating an X-ray focus, based on the combined actual position and a target position. In addition, the control loop also includes a plant for correcting a deviation of the position of the X-ray focus from the target position on the basis of the determined manipulated variable.

The regulation device according to embodiments of the present invention shares the advantages of the method according to embodiments of the present invention for regulating a position of an X-ray focus on the anode of an X-ray source of a scan unit of an X-ray imaging system.

The X-ray imaging system according to embodiments of the present invention, preferably a computed tomography system, has a scan unit with an X-ray source and an X-ray detector. The X-ray source and the X-ray detector are preferably part of a rotating imaging system. The X-ray imaging system according to embodiments of the present invention also has a control unit for controlling the rotating imaging system or the X-ray source and the X-ray detector and the regulation device according to embodiments of the present invention, which is used to control a position of an X-ray focus on an anode of the x-ray source. The X-ray imaging system according to embodiments of the present invention shares the advantages of the regulation device according to embodiments of the present invention.

Some of the components of the regulation device according to embodiments of the present invention can be designed for the most part in the form of software components. This applies in particular to parts of the plant model unit, the regulation unit and the plant. In principle, however, some of these components can also be implemented in the form of software-supported hardware, for example FPGAs or the like, especially when it comes to particularly fast calculations. Likewise, the required interfaces, for example if it is only a matter of transferring data from other software components, can be designed as software interfaces. However, they can also be designed as hardware-based interfaces that are controlled by suitable software.

A largely software-based implementation has the advantage that computer units or control units of X-ray imaging systems that have already been used can easily be retrofitted by a software update in order to work in the manner according to embodiments of the present invention. In this respect, the object is also achieved by a corresponding computer program product with a computer program which can be loaded directly into a memory device of a computer unit or a control unit of an X-ray imaging system and which includes program sections to carry out all steps to execute the method according to embodiments of the present invention when the computer program is executed in the computer unit or control unit of the X-ray imaging system.

In addition to the computer program, such a computer program product can optionally include additional components such as documentation and/or additional components, including hardware components such as hardware keys (dongles, etc.) for using the software.

A computer-readable medium, for example a memory stick, a hard disk or some other transportable or permanently installed data carrier, on which program sections of the computer program that can be read in and executed are stored, can be used for transport to the storage device of a computer unit of an X-ray imaging system and/or for storage on the computer unit of the X-ray imaging system. The computer unit can, for example, have one or more cooperating microprocessors or similar for this purpose.

Further, particularly advantageous configurations and developments of embodiments of the present invention result from the dependent claims as well as the following description and the figures, whereby the independent claims of one claim category can also be developed analogously to the dependent claims of another claim category and their description parts.

In the method according to embodiments of the present invention for regulating a position of an X-ray focus on the anode of an X-ray source of a scan unit of an X-ray imaging system, a detection of the position of the X-ray focus and a dead time for the detection of the position of the X-ray focus are preferably modeled by a plant model based on the deflection current as an input value. Hence, a model-based position of the X-ray focus is simulated. In addition, a model-based measurement position of the X-ray focus and the dead time that occurs when measuring the measurement position are also simulated. The two model-based quantities are preferably combined with one another. In the case of the model-based measurement position, information about the measurement process itself is also included.

The plant model is used to model a position, preferably a $\varphi$-position, of the X-ray focus on the basis of a deflection current. In addition, the measurement of the $\varphi$-position and/or the z-position in the slot is modeled with the measurement dynamics and with a dead time. The two model variables determined in this way are compared with the measured value of the $\varphi$-position and/or the z-position. The sum of the measured position, the model position and the negated value of the model position adjusted with the model of the measurement is used as the actual value for the regulation unit. The determination of the model value is advantageously adapted in time to the actual value measurement. If a measured value is available, it is compared with the model value generated delayed by the dead time. If there is no measured value, a model value can still be used to maintain the regulation. In this way, accelerated regulation and a shortened transition time during the jumps in the jump focus are achieved. This procedure is similar to how a Smith predictor works.

In the method, according to embodiments of the present invention, for regulating a position of an X-ray focus on the anode of an X-ray source of a scan unit of an X-ray imaging system, a path gain of a regulation unit and a path gain of the plant are particularly preferably adapted to the tolerances in the plant and the tolerances of measuring the actual values of the deflection current and the position of the X-ray focus. For the correct parameterization of the system model, the path gain and the gain of the regulation unit must be adapted to the real plant, since in reality there are tolerances in the plant. This adaptation takes place as follows: In a first measurement, the sizes of the measured value and the model value are determined at two different positions of the jump focus for the $\varphi$-direction and the z-direction. The difference between the respective measured values and model values at the two positions gives the jump distance. The path gain is now adjusted so that the jump distance of the measured values and the model values is the same.

In addition, in the method according to embodiments of the present invention, a filter can be used to suppress the influence of high-frequency interferences on the regulation unit. As later explained in detail, the filter only suppresses high-frequency interference that is not based on any actual change in the position of the jump focus. Such disturbances can occur, for example, due to irregularities in the anode plate or due to measurement noise. In the filter implementation, the model value or the value of the model-based measurement position is subtracted from the measured position, preferably the measured value of the $\varphi$-position and/or the z-position, of the X-ray focus, whereby a difference signal is formed. The high-frequency component of this difference signal is then extracted via a high-pass filter and then subtracted from the model value of the plant model, i.e. the combined actual position of the X-ray focus. In this way, high-frequency components of the measurement signal, which also result from the manipulated variable of the regulation unit and are mapped via the model, are visible to the regulation unit, because they occur simultaneously in the measurement and due to the subtraction of the model value from the measurement value before filtering and extraction by the high-pass filter, they are not captured by the high-pass filter. This means that only high-frequency components that are not generated by the regulation unit are filtered out. High-frequency interference, for example resulting from slits in the anode plate or high-frequency noise in the position measurement at a low radiation dose, is significantly reduced. As a result, the focus position remains significantly more stable and reproducible at the desired location on the anode plate during a single recording. Thus, any blurring in the imaging caused by the movement of the X-ray focus due to jump transitions and disturbances is significantly reduced.

In the method according to embodiments of the present invention, the X-ray focus is very particularly preferably controlled as a jump focus with a predetermined trajectory of the position of the X-ray focus on the anode of the X-ray source. During the jump, there is preferably either a change in the $\varphi$-position or a change in the z-position of the jump focus. It is very particularly preferable that the $\varphi$-position of the jump focus and the z-position of the jump focus are alternately changed. The jump focus also preferably jumps back and forth between four positions.

Also preferably, in the method according to embodiments of the present invention the position of the X-ray focus comprises a $\varphi$-position and a z-position and a geometric decoupling of the detection of the $\varphi$-position and the z-position is carried out. The coupling problem is that a change in the z-position causes a change in the $\varphi$-position in the detection system. During decoupling, an actual $\varphi$-position of the X-ray focus is calculated on the basis of the measured $\varphi$-position and the measured z-position, with the geometric coupling being compensated. This function can be used to determine the target value for the $\varphi$-position as well as to determine the actual value for the $\varphi$-position. The offset value of the $\varphi$-position is determined as the correction value for decoupling. This can be calculated in an adjustment step. For this purpose, the values of the measured positions and the model positions are determined for two $\varphi$-positions and two z-positions. An adjusted offset value can be calculated from the differences in the mean values of the $\varphi$-positions and the distance in the z-direction. Disturbances in the $\varphi$-position of the X-ray focus, which consist of jumps in the z-direction, are thus significantly reduced or eliminated.

During decoupling, the corrected offset value is subtracted from the $\varphi$-position of the X-ray focus. In addition, a distance between two z-positions of the X-ray focus is corrected to a corrected z-distance by a correction function and multiplied by a z-position of the X-ray focus. Finally, the result is multiplied by the result of the subtraction of the offset value from the $\varphi$-position, the decoupled $\varphi$-position being the end result.

The method according to embodiments of the present invention is very particularly preferably designed in such a way that it is dynamically switched between the operation of a control of the position of the X-ray focus on the X-ray detector and the operation of a regulation of the position of the X-ray focus. In our nomenclature "control" of a position means an open loop control. In contrast thereto, "regulation"

means a closed loop control. Hence, the mentioned advantageous improvement in the regulation of a jump focus is also extended to the open looped controlled mode. The plant model is also used for such a mixed regulated/controlled operation, since it depicts the behavior of the plant both dynamically and stationary. For example, in the case of so-called beam blanking, the position can continue to be pre-controlled in the time ranges, in which no tube current is flowing, and therefore no position of the X-ray focus can be measured, so that it can be adjusted very quickly, when the X-ray beam is subsequently switched on. The controlled mode can also be used for recordings with a very low X-ray dose. In such a case, the X-ray dose may not be sufficient to capture the position of the X-ray focus. When switching from regulated to open-loop operation, only the model value of the φ-position and/or the z-position is used as the position signal for the regulation unit. The measured value of the φ-position and/or the z-position and the corresponding modeled measured value are each set to the value 0. In addition, a stationary offset value of the model value of the φ-position must be added. This offset value corresponds to the value of the difference between the measured value of the φ-position and the modeled measured value of the φ-position at the time of switchover between the two different modes. If you want to switch back to regulated operation, you have to switch back to the original structure. This means that during the operation of a control, the measured values and model-based measured values for the position of the X-ray focus that are only determined during closed-loop operation are set to the value "0". In order to calculate a correct offset value of the φ-position, these measured values are required again when changing to regulation i.e. the closed-loop operation. The zero values for the measured value and the model-based measured value are therefore reset during the transition to regulated operation.

In the case of controlled operation, the position of the jump focus can advantageously be kept relatively stable, even if the position measurement is temporarily not available. When using beam blanking in combination with position regulation according to embodiments of the present invention, a stable position of the X-ray focus can be achieved again very quickly after the electron beam is switched on again thanks to the controlled operation while the X-ray beam is switched off. Both options thus lead to an optimal imaging with little motion blur.

In order to determine the model-based position of the x-ray focus, the plant model unit of the above-mentioned regulation device according to embodiments of the present invention is preferably set up to simulate and/or combine a model-based position of the x-ray focus and/or a model-based measurement position of the x-ray focus and a dead time of the measurement of the model-based measurement position of the x-ray focus by a plant model of a regulation path, i.e. a plant, based on the deflection current.

As already explained in connection with the corresponding method, the plant model is used to model a position, preferably a φ-position, of the x-ray focus on the basis of a deflection current. In addition, the measurement of the φ-position in the slot is modeled using the measurement dynamics and a dead time. The two model variables determined in this way are compared with the measured value of the φ-position. The sum of the measured position, the model position and the negated value of the model position adjusted with the model of the measurement is used as the actual value for the regulating unit.

As already explained in connection with the corresponding method, the determination of the model value is advantageously adapted in terms of time to the actual value measurement. If a measured value is available, this is compared with the model value generated delayed by the dead time. If no measured value is available, a model value can still be used to maintain the regulation. In this way, accelerated regulation and a shortened transition time during the jumps of the jump focus are achieved.

BRIEF DESCRIPTION OF THE DRAWINGS

The present invention is explained in more detail below with reference to the attached figures on the basis of example embodiments. The same components are provided with identical reference numbers in the various figures.

FIG. 8 shows the decoupling unit, shown in FIG. 5, in detail, FIG. 9 shows a detailed illustration of a coupling of an X-ray beam in the φ-direction and in the z-direction, FIG. 10 shows a flow chart to illustrate a method for regulating a control of a position of an X-ray focus of an X-ray source of a medical imaging device according to an example embodiment of the present invention, FIG. 11 shows a representation of measurement curves, difference curves of the measured value and the model value of the φ-coordinate and the z-coordinate of an X-ray focus.

DETAILED DESCRIPTION

Figure 1:
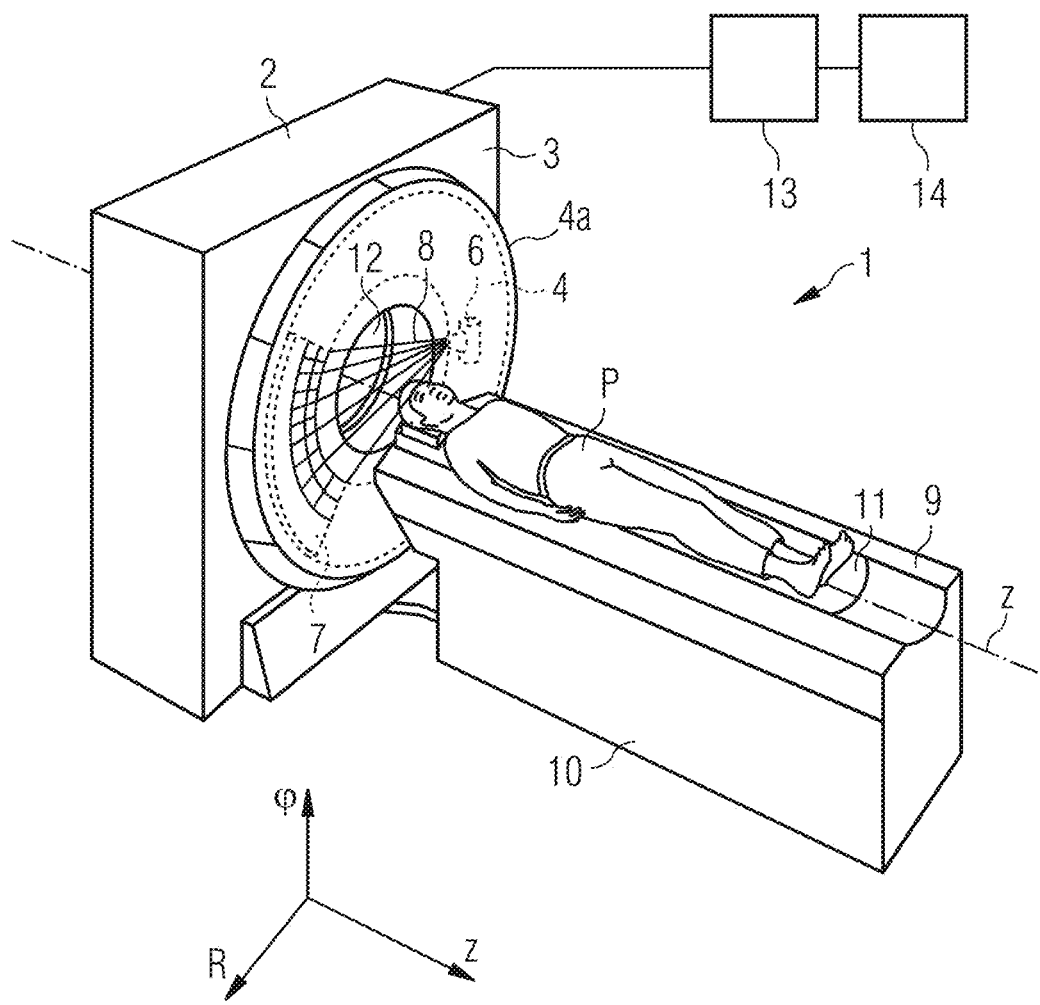
FIG. 1 shows a schematic representation of a computed tomography system.

FIG. 1 shows a schematic representation of a computed tomography system 1 in order to clarify its general structure. The arrangement comprises a gantry 2 with a stationary part 3, also referred to as a gantry frame, and with a part 4 which can be rotated or rotated about a system axis z, also referred to as a rotor or drum. The rotating part 4 has an imaging system (X-ray system) 4a, which comprises an X-ray source 6 and an X-ray detector 7, which are arranged opposite one another on the rotating part 4. The X-ray source 6 and the X-ray radiation detector 7 together form the imaging system 4a. When the computed tomography system 1 is in operation, the X-ray source 6 emits X-rays 8 in the direction of the X-ray detector 7, penetrates a measurement object P, for example a patient P, and is detected by the X-ray detector 7 in the form of measurement data or measurement signals.

In FIG. 1, a patient bed 9 for positioning the patient P can also be seen. The patient bed 9 comprises a bed base 10 on which a patient support plate 11 provided for the actual positioning of the patient P is arranged. The patient support plate 11 can be adjusted relative to the bed base 10 in the direction of the system axis z, i.e. in the z direction, in such a way that, together with the patient P, it can be introduced into an opening 12, i.e. a patient reception area 12 of the gantry 2 for recording X-ray projections from the patient P.

The computational processing of the X-ray projections recorded with the imaging system 4a or the reconstruction of slice images, 3D images or a 3D data set based on the measurement data or measurement signals of the X-ray projections takes place in an image computer 13 of the computed tomography system 1, wherein the slice images or 3D images can be displayed on a display device 14. The image computer 13 can also be designed as a control unit for controlling an imaging process for controlling the gantry 2 and in particular the imaging system 4a.

Figure 2:
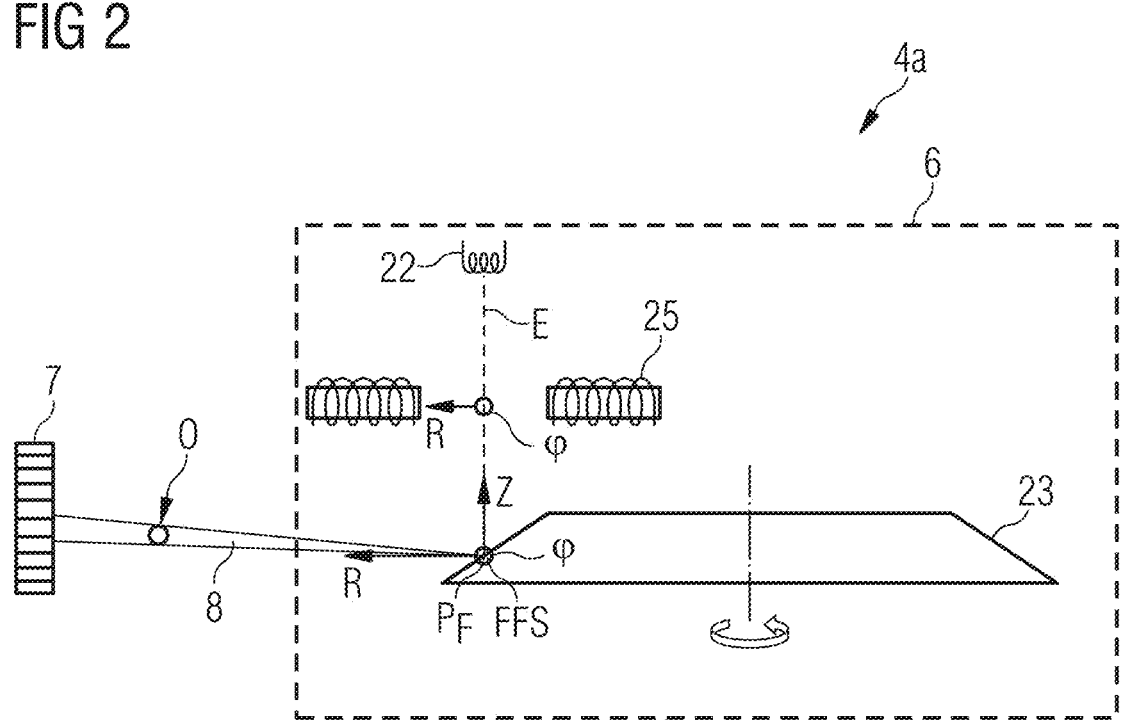
FIG. 2 shows a schematic representation of an X-ray source of a computed tomography system.

FIG. 2 shows a sectional illustration of an arrangement of an imaging system 4a with an X-ray source 6, which is framed with dashed lines, and an X-ray detector 7. The X-ray source 6 comprises a cathode 22 from which an electron beam E is emitted in the z-direction. The electron beam E is focused and deflected by a deflection unit 25, which is designed as an electromagnetic deflection coil. Furthermore, the electron beam E strikes a rotatable mounted anode 23, which can be rotated about the z-axis. When the X-ray source 6 is in operation, the anode 23 is set in rotation by an electric drive (not shown). When the X-ray source 6 is in operation, an electrical high voltage is applied between the cathode 22 and the anode 23, so that the aforementioned electron beam E emanates from the cathode 22 and acts on the anode 23. So that the anode 23 is acted upon in its edge area by the electron beam E at a predetermined position PF, the position of the X-ray focus FFS, which can be clearly described with a $\varphi$-coordinate and a z-coordinate, the electron beam E is appropriately deflected by the deflection unit 25. The electron beam E strikes the material of the anode 23 and there forms the already mentioned focal spot or X-ray focus FFS.

The resulting X-ray radiation 8 emerges laterally from the X-ray source 6 via an exit window. An object O between the X-ray source 6 and the detector 7 is also shown in FIG. 2. The object O is acted upon by the X-ray beam 8 and casts a shadow on the X-ray detector 7. The position of the electrical focal spot FFS is generally influenced by different disturbance variables during operation. To compensate for a focal spot movement caused by these disturbance variables, the electromagnetic deflection unit 25 generates a correspondingly oppositely directed, time-variable deflection field. For this purpose, the electromagnetic or electrostatic deflection unit 25 is connected to a control unit (not shown), which provides control signals that take place in accordance with previously recorded correlations that characterize the focal spot movement as a function of the operating parameters of the electric drive not shown in FIG. 2. As already mentioned, a movement of the focal point can also be desired and deliberately controlled, if a so-called jump focus is to be generated. In this case, the control unit controls a change in the position PF of the X-ray focus FFS in the $\varphi$-direction and in the z-direction as a function of time.

Figure 3:
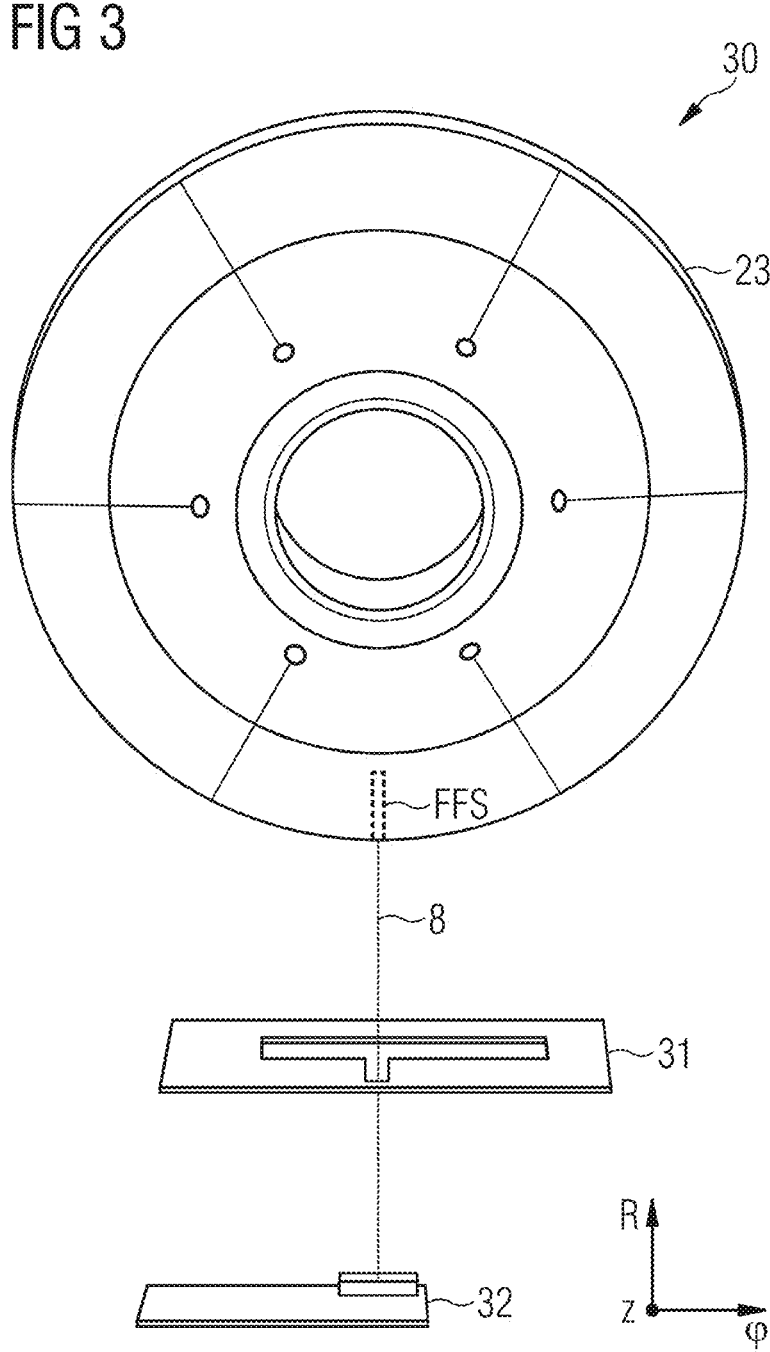
FIG. 3 shows an arrangement for measuring a φ-component and a z-component of an X-ray beam.

In FIG. 3, an arrangement 30 for measuring a $\varphi$-component and a z-component of an X-ray focus FFS of an X-ray beam 8 is shown schematically. The arrangement 30 includes the anode 23, also referred to as a plate. A secondary component of the X-ray beam 8 reflected by the anode 23 is guided through a slot 31 in the x-ray beam shielding and detected by a so-called position element 32. In order to realize a jump focus FFS, the coordinates $\varphi$ and z of the point of incidence of the X-ray beam 8, i.e. the X-ray focus FFS, are varied.

Figure 4:
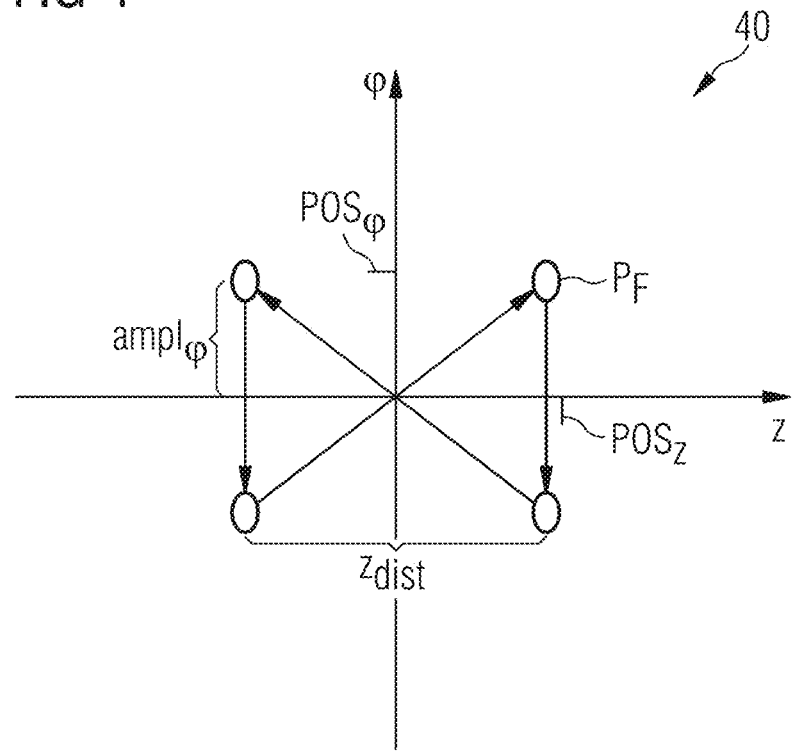
FIG. 4 shows a representation of a jump focus in the φ-z plane.

In FIG. 4, the movement of the jump focus FFS is illustrated. The jump focus FFS changes its position PF on the anode in a defined time interval. Either the $\varphi$-position POS$\varphi$ or the z-position POSz of the X-ray focus FFS or both coordinates POS$\varphi$, POSz are changed at the same time. The jump amplitude ampl$\varphi$ in the p-direction indicates the change in the p-position POS$\varphi$ of the X-ray focus FFS during a jump, the z-distance zdist indicates the change in the z-position during a jump.

Figure 5:
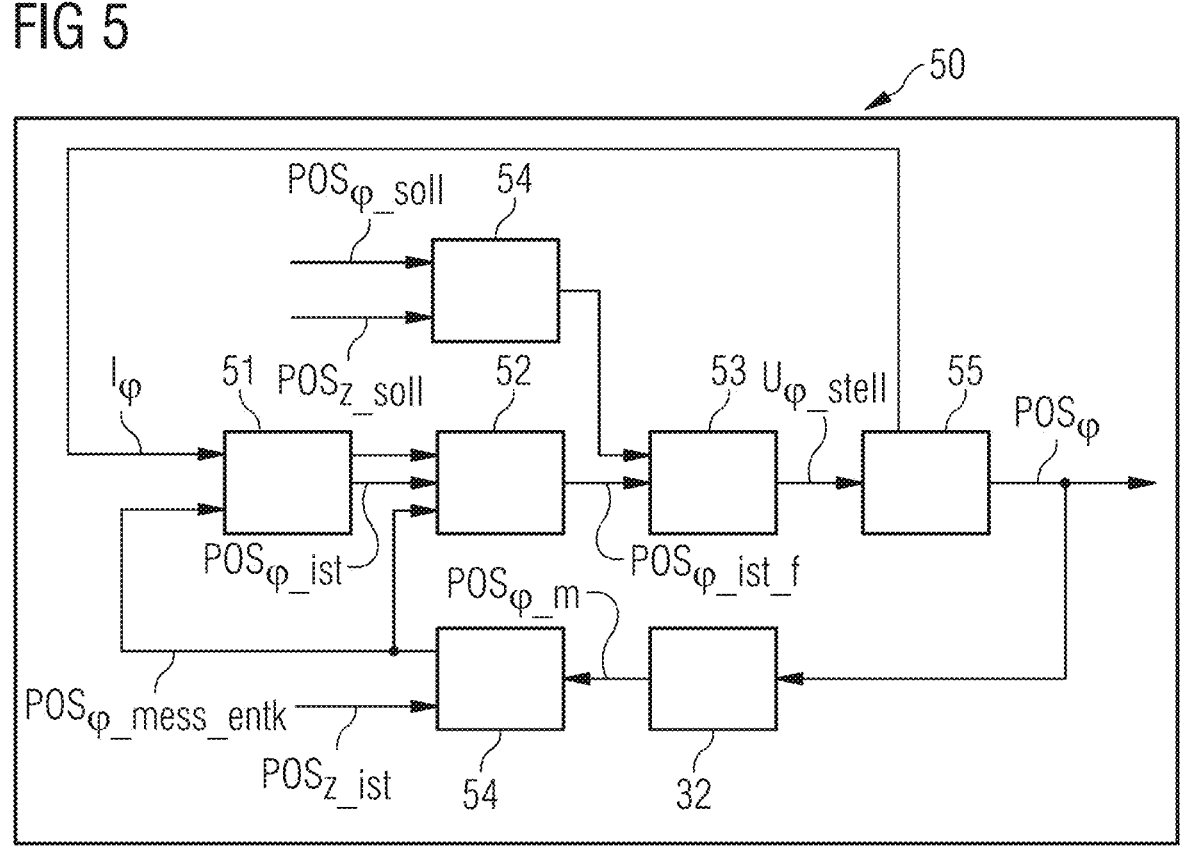
FIG. 5 shows a schematic representation of a regulation device according to an example embodiment of the present invention.

FIG. 5 shows a schematic representation of a position regulation device 50 according to an example embodiment of the present invention. The position regulation device 50 comprises a single-loop control loop with a single plant, i.e. regulation path. The control loop comprises a plant model unit 51, which records both an electrical current I$\varphi$ for deflecting the X-ray beam 8 in the p-direction and a decoupled p-position POS$\varphi$_mess_entk as input variables. The input variables, the current I$\varphi$ and the decoupled p-position POS$\varphi$_mess_entk, are processed by the plant model unit 51. On the basis of the input variables I$\varphi$, POS$\varphi$_mess_entk, the plant model unit 51 generates a possibly modeled actual variable POS$\varphi$_ist which is then passed through a slot filter 52.

The slot filter 52 serves to suppress the influence of high-frequency interference on the following position regulating unit 53 and is explained in detail in connection with FIG. 7.

In addition to the filtered input variable POS$\varphi$_ist_f, the position regulating unit 53 also receives two target values POS$\varphi$_soll, POSZ_soll from a $\varphi$-z decoupling unit 54, which performs a $\varphi$-z decoupling according to equation (2) (see below). The two target values POS$\varphi$_soll, POSZ_soll represent the target p-position POS$\varphi$_soll of the X-ray beam and the target z-position POSZ_soll of the X-ray beam. The position regulating unit 53 determines on the basis of the processing of the target values POS$\varphi$_soll, POSZ_soll and the decoupled actual values POS$\varphi$_mess_entk, POSz_ist a manipulated variable, namely the necessary coil voltage U$\varphi$_stell, which is applied to the magnetic coil of the electromagnetic deflection unit 25 (see FIG. 2) in order to achieve the target values POS$\varphi$_soll, POSZ_soll.

The $\varphi$-position POS$\varphi$ of the jump focus FFS is now corrected on the plant 55.

The position element 32 (please refer to FIG. 3) then carries out a measurement of the position of the X-ray focus FFS, the measured $\varphi$-position POS$\varphi$_mess being determined, which has not yet been decoupled.

This not yet decoupled $\varphi$-position POS$\varphi$_mess is input together with a measured z-position POSZ_ist into a decoupling unit 54, which uses this to determine a decoupled $\varphi$-measurement position POS$\varphi$_mess_entk according to equation (2).

The decoupled $\varphi$-measurement position POS$\varphi$_mess_entk is transmitted to the plant model unit 51, which processes this decoupled $\varphi$-measurement position POS$\varphi$_mess_entk together with the current I$\varphi$ of the deflection coil in the manner described above. The decoupled $\varphi$-measurement position POS$\varphi$_mess_entk is also transmitted directly to the slot filter 52.

Figure 6:
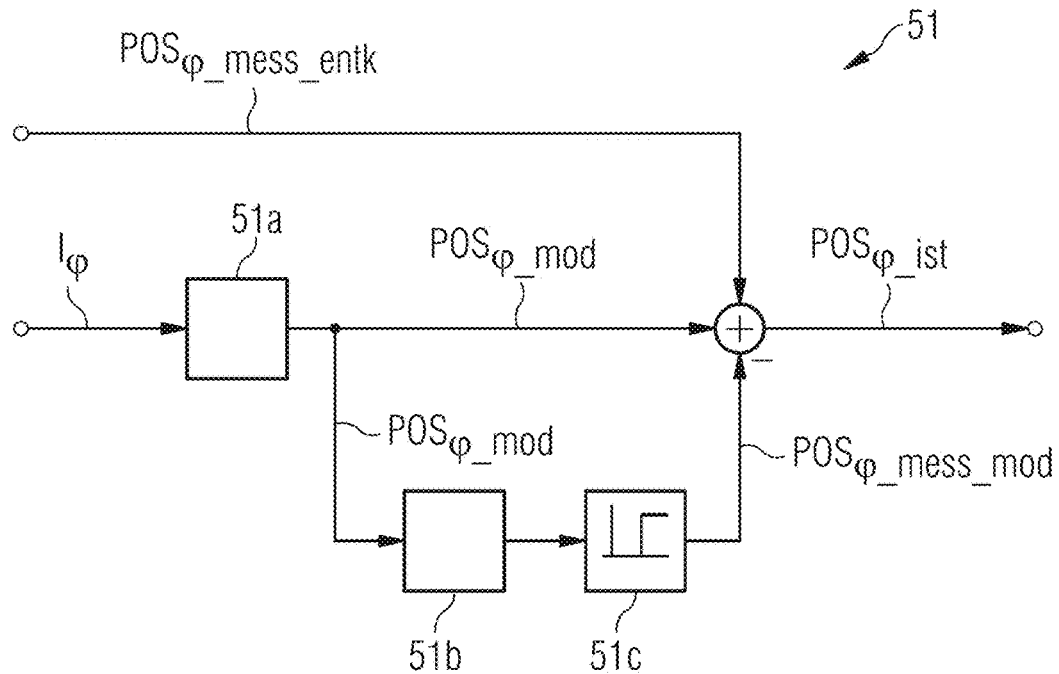
FIG. 6 shows a schematic representation of a plant model shown in FIG. 5.

FIG. 6 shows the plant model unit 51 shown in FIG. 5 in detail. First, based on the deflection current I$\varphi$, a model-based $\varphi$-position POS$\varphi$_mod is calculated using a plant model 51a. In addition, the measurement in the slot with dead time is simulated by a measuring plant model 51b and a dead time simulation unit 51c and a simulated measured variable POS$\varphi$_mess_mod of the $\varphi$-position, also referred to as the model-based measurement position, is determined. These two variables POS$\varphi$_mod, POS$\varphi$_mess_mo are offset against the measured and already decoupled $\varphi$-position value POS$\varphi$_mess_entk in the following way:

$$POS_{\varphi\_ist} = POS_{\varphi\_mess\_entk} + POS_{\varphi\_mod} - POS_{\varphi\_mess\_mod}. \quad (1)$$

The calculation method is similar to the classic Smith predictor. The result, i.e. the actual φ-position POSφ_ist, is used after filtering, which is illustrated in FIG. 7, in filtered form as the actual value for the position regulating unit 53. For low-frequency or constant components of the signal, the model-based φ-position POSφ_mod is the same as the model-based φ-measurement position POSφ_mess_mod. In this case, only the decoupled φ-measurement position remains in equation (1) as the actual φ-position POSφ_ist=POSφ_mess_entk. For high-frequency signal components, these components are reduced in the measurement due to the filter characteristics in the position detection. This means that they are also reduced in the model-based φ-measurement position POSφ_mess_mod. In this case, the proportions in the model-based φ-position POSφ_mod are transferred directly to the actual φ-position POSφ_ist.

Figure 7:
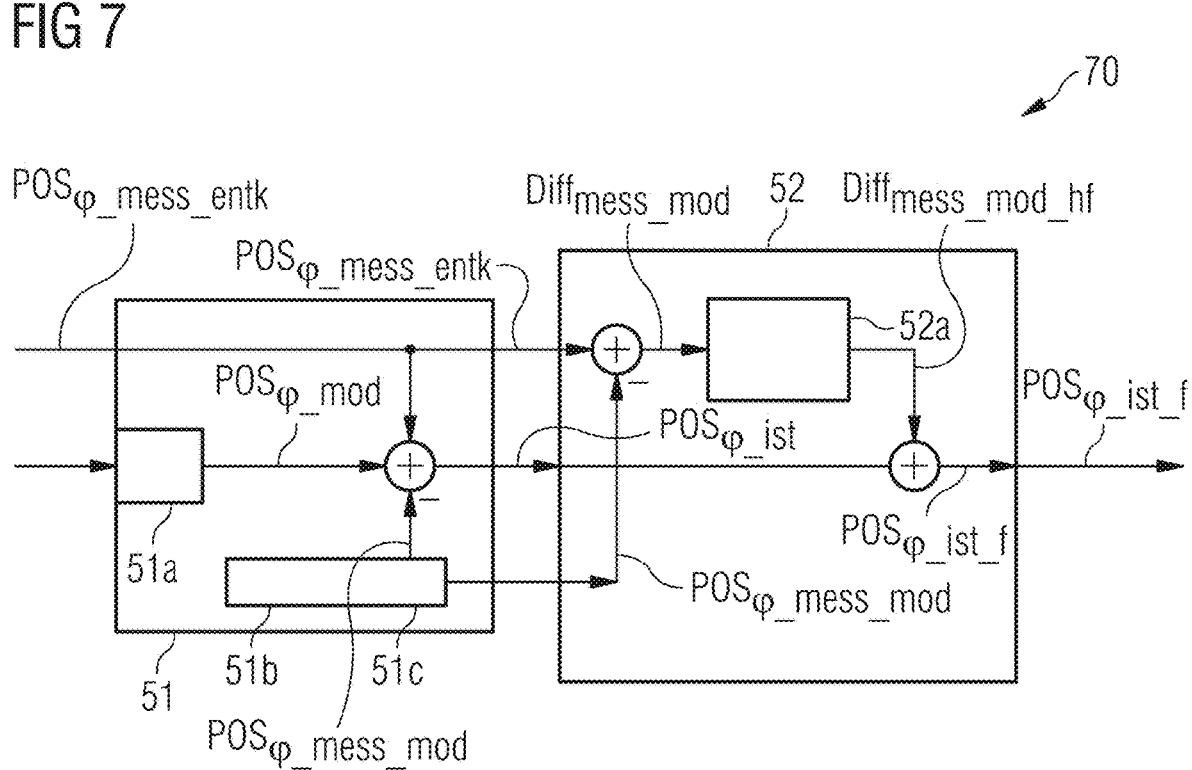
FIG. 7 shows the slot filter, already shown in FIG. 5, in detail.

FIG. 7 shows an arrangement 70, which illustrates the slot filter 52 already shown in FIG. 5 in detail in cooperation with the adjacent or upstream plant model unit 51. The plant model unit 51 generates, as explained in connection with FIG. 6, an actual φ-position value POSφ_ist and also outputs the φ-position value or the decoupled φ-measurement position POSφ_mess_entk as well as the simulated measured variable of the φ-position POSφ_mess_mod. In the measured values POSφ_mess_entk of the φ-position of the X-ray focus FFS, regular dips and overshoots occur due to slits in the anode plate structure. These act as high-frequency interference on the control loop. Even with low X-ray intensity, the measurement noise causes high-frequency interference that is not based on any actual change in the position of the X-ray focus FFS. Without filtering, such disturbances would lead to reactions of the control loop, which would then lead to an actual movement in the position of the X-ray focus FFS and thus to movement artifacts.

Therefore, the φ actual value POSφ_ist generated by the plant model unit 51 and possibly modeled as well as the decoupled measured φ-position value POSφ_mess_entk and the simulated measured variable POSφ_mess_mod of the φ-position are transferred to the slot filter 52. The two values, i.e. the measured and decoupled φ-position value POSφ_mess_entk and the simulated measured variable POSφ_mess_mod of the φ-position, are subtracted in the slot filter 52. The result Diffmess_mod corresponds to the deviation of the model from reality and includes both low-frequency and high-frequency components. With the high-frequency components of the measurement signal POSφ_mess_entk, the difference signal Diffmess_mod includes the actual errors due to irregularities in the rotating anode or high-frequency interference due to the measurement noise. The high-frequency component Diffmess_mod_hf is extracted from this variable Diffmess_mod via a high-pass filter 52a, which is part of the slot filter 52, and subtracted from the possibly modeled actual φ-value POSφ_ist. The possibly modeled actual φ-value POSφ_ist_f, which has been corrected for high-frequency interference effects, is then transmitted to the position regulating unit 53.

FIG. 8 shows the decoupling unit 54 shown in FIG. 5 in detail. An actual decoupled φ-position POSφ_entk is calculated from the measured or as target position predetermined φ-position POSφ and the measured or predetermined z-position POSz of the X-ray focus FFS by compensating the geometrical coupling. This decoupling unit 54 is used for both the target value path and the actual value path. For decoupling, an offset φZero_Offset, which is calculated in the manner described in connection with FIG. 9, is subtracted from the φ-position POSφ.

In addition, a reciprocal value zdist_rec of a measured or predetermined distance between two z-positions zdist is calculated and this reciprocal value zdist_rec is multiplied by a z-position POSz that is either measured or predetermined as a target position. The result is then multiplied by the result from the subtraction of the offset φZero_Offset from the φ-position POSφ, the decoupled φ-position POSφ_entk being the end result.

The offset value φZero_Offset of the φ-position POSφ is therefore required as a correction value for the decoupling function. This offset value φZero_Offset can be calculated in an adjust step. For this purpose, the values of the measured position and the model position are determined again for two φ-positions and two z-positions. An offset value φZero_Offset can then be calculated from the differences between the mean values of the φ-positions and the distance in the z-direction (see also FIG. 9).

FIG. 9 shows a detailed illustration 90 of a coupling of an X-ray beam in the φ-direction and in the z-direction. In FIG. 9, four jump positions FFS of an X-ray focus are shown. These jump positions differ from each other regarding z-position, R-position and φ-position. Due to a coupling of the deflection in the φ-direction and in the z-direction, a φ-coordinate of the x-ray beam is incorrectly detected by the position element 32. This false decoupling is symbolized in FIG. 9 by four false decoupled jump positions FFSFD1, FFSFD2, FFSFD3, FFSFD4. For comparison, also the four correctly decoupled positions FFSCD1, FFSCD2, FFSCD3, FFSCD4 are shown in FIG. 9. Further, in FIG. 9, also two not decoupled positions FFSND1, FFSND2 of the jump focus are drawn in.

A correction, a so-called φZero-Offset, results from the following equation:

$$\varphi_{Zero\_Offst} = \varphi_{Zero\_Offset\_old} - r_{dist} \cdot \frac{(aw_{pz\_1234})}{(ampl_R)}. \tag{2}$$

The new φZero_Offset is calculated from the old φZero_Offset old at the last jump position reduced by the quotient from the φ-deviation awpz_1234 between incorrectly decoupled jump position FFSFD1, FFSFD2, FFSFD3, FFSFD4 and correctly decoupled jump position FFSCD1, FFSCD2, FFSCD3, FFSCD4 and the R-amplitude amplR of the jump focus multiplied by the distance rdist of the jump focus FFS to the slot 31 in the X-ray shield. The R-amplitude results from the z-jump zdist explained in connection with FIG. 4 and FIG. 8, i.e. the distance between two z-positions. Since the geometry of the anode 23 is known, the R-amplitude amplR results from the z-jump zdist in an unambiguous manner. The formula (2) results from the second set of rays, where the quotient of the R-amplitude amplR and the distance rdist of the jump focus FFS to the slot 31 is equal to the quotient of the φ-deviation awpz_1234 and the new φZero_Offset.

FIG. 10 shows a flowchart 1000 to illustrate a method for regulating a control of a position of an X-ray focus of an X-ray source of a medical-technical imaging device according to an example embodiment of the present invention. In step 10.I, an actual variable POSφ_ist is initially modeled on the basis of a measured deflection current Iφ and an already decoupled measurement position POSφ_mess_entk. In step 10.II, the influence of high-frequency interference on the regulation process is suppressed, a filtered actual variable POSφ_ist_f being determined. For details of the filtering, reference is made to the description of FIG. 6. In step 10.III, the desired variables POSφ_soll, POSz_soll are decoupled in the manner described in connection with FIG. 8 and FIG. 9.

In step 10.IV, a position regulation is carried out on the basis of the actual variable POSφ_ist and the decoupled desired variable POSφ_soll entk of the φ-position, i.e. the manipulated variable, an electrical voltage Uφ_stell used to generate the deflection current Iφ, is calculated and is played out on plant 55 in step 10.V. In step 10.VI a position measurement is carried out and a measured φ-position POSφ_mess is determined. In step 10.VII, a φ-z-decoupling is then carried out on the basis of the measured φ-position POSφ_mess and a measured z-position POSZ_ist, as it was explained in connection with FIG. 8 and FIG. 9. In step 10.VIII the decoupled measured φ-position POSφ_mess_entk is made available for steps 10.I and 10.II. The regulation process then continues with step 10.I.

FIG. 11 shows a representation 110 of measurement curves POSφ_mess, POSz mess and difference curves DIFFφ_mess_mod, DIFFz_mess_mod regarding the difference between the measured value and the model value of the position of an X-ray focus.

When measuring a measured value POSφ_mess, POSz mess of the position of an X-ray focus, the following parameters, which have a relevant influence on the position regulation of the X-ray focus and on the φ-z-decoupling illustrated in FIG. 8 and FIG. 9, are subject to a tolerance:
the gain of the φ-position POSφ with a linear error>=+−10%,
the gain of the z-position POSz with a linear error>=+−10% and
the offset value φZero_Offset of the φ-position POSφ to the zero-position in the X-ray source for the current Iφ=0 amperes.

In order to compensate for the influence of the parameter variations, the following parameters should be adjusted by the plant model unit 51 and the regulation unit 53:
the offset value φZero_Offset,
the gain of the plant model unit 51 and the regulation unit 53 with respect to the φ-position POSφ and
the gain of the plant model unit 51 and the regulation unit 53 with respect to the z-position POSz.

The adjustment can take place in a single adjustment step before an imaging process or by continuous adaptation during an imaging process.

In the plant model unit 51 (see FIG. 6), an intermediate variable is calculated from a difference DIFFφ_mess_mod between a measured value POSφ_mess_entk and a model value or a model measured value POSφ_mess_mod, which reflects the difference between measurement and model. The accuracy of the model can be determined from this variable DIFFφ_mess_mod, when the position of the X-ray focus changes. One object of the regulation is that this deviation of the model from the measurement is minimized so that the model is completely adapted. FIG. 11 shows curves for a so-called φ-z jump scan, with all four positions of the jump focus being approached.

When determining the above-mentioned parameters, sum values sump_1, sump_2, sump_3, sump_4, sumz_1, sumz_2 are determined via sum times tsum_p, tsum_z on the plateaus of the difference curves DIFFφ_mess_mod, DIFFz_mess_mod. "p" is the short form of "phi" or "φ". Sums can also be converted directly into mean values, the mean values being determined by dividing the respective sums by the respective number of measured values. Between the sum times tsum_p, tsum_z there are waiting times twt during which transitions between the φ-positions and z-positions of the jump focus take place. The differences can be summed up and averaged over several readout sequences. The aim of the adaptation is that the difference curves DIFFφ_mess_mod, DIFFz_mess_mod become smooth apart from external disturbance variables. Then the difference between model and measurement is minimal and the system is optimally adapted.

First, mean values are calculated from the sum values:

$$mwp\_x = sump\_x / tsum\_p,$$

$$mwz\_x = sumz\_x / tsum\_z.$$

In that context is x an integer between 1 and 4 or 1 and 2. Further, x is a number that reflects the position in φ and z in the sequence shown.

Second, the mean values of a readout sequence are calculated:

$$mwp\_12 = (mwp\_1 + mwp\_2)/2,$$

$$mwp\_34 = (mwp\_3 + mwp\_4)/2,$$

$$mwp\_1234 = (mwp\_1 + mwp\_2 + mwp\_3 + mwp\_4)/4,$$

$$mwz\_12 = (mwz\_1 + mwz\_2)/2.$$

Third, the deviations of the mean values are calculated:

$$awp\_12 = (mwp\_1 - mwp\_12)/2 + (mwp\_12 - mwp\_2)/2,$$

$$awp\_34 = (mwp\_3 - mwp\_34)/2 + (mwp\_34 - mwp\_4)/2,$$

$$awp\_1234 = (awp\_12 + awp\_34)/2,$$

$$awpz\_1234 = (mwp\_12 - mwp\_1234)/2 + (mwp\_1234 - mwp\_34)/2,$$

$$awz\_12 = (mwz\_1 - mwz\_12)/2 + (mwz\_12 - mwz\_2)/2.$$

In a fourth step, the correction variables sppgainp_korr, kp_korr for the gain of the plant model unit 51 and the regulation unit 53 are calculated in φ:
There are the following parameters for this:
the jump amplitude amplφ,
the correction factor for the gain of the plant model unit 51 of φ: sppgainp_korr,
the correction factor for the gain of the regulation unit 53 of φ: kp_korr.

Then, the correction factor for the gain of the plant model unit 51 for φ results in:

$$sppgainp\_korr = (awp\_1234 + amplφ)/amplφ.$$

The correction factor for the gain of the regulation unit 53 of φ results in:

$$kp\_korr = amplφ/(awp\_1234 + amplφ) = 1/sppgainp\_korr.$$

Fifth, the correction variables sppgainz_korr, zp_korr for the amplification of the plant model unit 51 and the regulation unit 53 are calculated for z:
There are the following parameters for this:
the jump ampitude amplz,
the correction factor for the gain of the plant model unit 51 of z: sppgainz_korr,
the correction factor for the gain of the regulation unit 53 of z: kz_korr.

Then the correction factor for the amplification of the plant model unit 51 of z results as follows:

$$sppgainz\_korr = (awz\_12 + amplz)/amplz.$$

The correction factor for the gain of the regulation unit 53 of z results from:

$$kz\_korr = amplz/(awz\_12 + amplz) = 1/sppgainz\_korr.$$

Sixth, the new offset value φZero-Offset is now calculated according to equation (2).

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been disclosed in the form of embodiments and variations thereon, it will be understood that numerous additional modifications and variations could be made thereto without departing from the scope of the present invention.

Finally, it is pointed out once again that the methods and regulation devices described in detail above are only example embodiments, which can be modified in various ways by the person skilled in the art without departing from the scope of the present invention. Furthermore, as mentioned above, the use of the indefinite article "a" or "an" does not exclude the possibility of the relevant characteristics appearing more than once. Likewise, the term "unit" does not exclude the fact that the relevant component consists of several interacting sub-components, which may also be spatially distributed.

What is claimed is:

1. A method for regulating a position of an X-ray focus on an anode of an X-ray source of an X-ray imaging system, the method comprising:
   determining a combined actual position of the X-ray focus by combining a measured position of the X-ray focus and a model based position of the X-ray focus, the model based position of the X-ray focus determined based on a measured value of a deflection current;
   determining a manipulated variable based on the combined actual position and a target position; and
   performing a regulation for correcting a deviation of the position of the X-ray focus from the target position based on the manipulated variable.

2. The method according to claim 1, further comprising:
   determining the model based position of the X-ray focus by at least one of
      calculating a model based position of the X-ray focus or a model based measurement position of the X-ray focus, wherein a dead time of a measurement of the model based measurement position of the X-ray focus is considered when calculating the model based measurement position of the X-ray focus, or
      combining the model based position of the X-ray focus and the model based measurement position of the X-ray focus; wherein
   the at least one of the combining or calculating is performed by a plant model of a plant based on the deflection current.

3. The method according to claim 2, further comprising:
   performing an adaption of a regulation gain of a regulation unit and of a path gain of the plant to tolerances in the plant and during measurement of the deflection current and of the position of the X-ray focus.

4. The method according to claim 3, further comprising:
   determining a filtered combined actual position by filtering the combined actual position of the X-ray focus to suppress an influence of high-frequency interference on the regulation unit, wherein the filtering includes
      determining a difference signal by subtracting the model based measurement position from the measured position of the X-ray focus,
      extracting a high-frequency component of the difference signal by high-pass filtering, and
      subtracting the high-frequency component of the difference signal from the combined actual position of the X-ray focus.

5. The method according to claim 4, further comprising:
   dynamically switching between operation of a control of the position of the X-ray focus and operation of a regulation of the position of the X-ray focus.

6. The method according to claim 3, wherein the X-ray focus is controlled as a jump focus with a trajectory of the position of the X-ray focus on the anode of the X-ray source.

7. The method according to claim 3, further comprising:
   dynamically switching between operation of a control of the position of the X-ray focus and operation of a regulation of the position of the X-ray focus.

8. The method according to claim 2, wherein the X-ray focus is controlled as a jump focus with a trajectory of the position of the X-ray focus on the anode of the X-ray source.

9. The method according to claim 2, further comprising:
   dynamically switching between operation of a control of the position of the X-ray focus and operation of a regulation of the position of the X-ray focus.

10. The method according to claim 1, wherein the X-ray focus is controlled as a jump focus with a trajectory of the position of the X-ray focus on the anode of the X-ray source.

11. The method according to claim 10, wherein
    the position of the X-ray focus includes a φ-position and a z-position, and
    a geometric decoupling of an acquisition of the φ-position and the z-position is carried out.

12. The method according to claim 11, further comprising:
    determining, for calculation of the decoupled φ-position, a corrected offset value of the φ-position of the X-ray focus based on a jump amplitude in the R-direction, a deviation of an average of measurement values of the φ-position and the z-position of the X-ray focus and a previous offset value.

13. The method according to claim 12, wherein the decoupled φ-position is determined by
   subtracting the corrected offset value of the φ-position,
   determining a product by multiplication of a recursive value of a distance between two z-positions with the z-position, and
   multiplying the product with a result of the subtracting the corrected offset value.

14. The method according to claim 1, further comprising:
   dynamically switching between operation of a control of the position of the X-ray focus and operation of a regulation of the position of the X-ray focus.

15. A non-transitory computer program product with a computer program, which can be loaded into a storage unit of a control unit of an X-ray imaging system, the computer program including program sections that, when executed by the control unit, cause the X-ray imaging system to carry out the method according to claim 1.

16. A non-transitory computer-readable medium storing program sections that, when executed by a computer unit, cause the computer unit to perform the method of claim 1.

17. A regulation device to regulate a position of an X-ray focus on an anode of an X-ray source of an X-ray imaging system, the regulation device comprising:
   a plant model unit to determine a combined actual position of the X-ray focus by combining a measured position of the X-ray focus and a model based position of the X-ray focus, the model based position of the X-ray focus determined based on a measurement value of a deflection current;
   a regulation unit to generate a manipulated variable based on the combined actual position and a target position; and
   a plant to correct a deviation of the position of the X-ray focus from the target position based on the manipulated variable.

18. The regulation device according to claim 17, wherein the plant model unit is configured to determine the model based position of the X-ray focus by at least one of calculating or combining, by a plant model of a plant based on the deflection current, (i) at least one of a model based position of the X-ray focus or a model based measurement position of the X-ray focus and (ii) a dead time of the measurement of the model based measurement position of the X-ray focus.

19. An X-ray imaging system, comprising:
   an X-ray source;
   an X-ray detector;
   a control unit to control the X-ray source and the X-ray detector; and
   the regulation device according to claim 17, to regulate a position of an X-ray focus of an anode of the X-ray source.

20. A regulation device to regulate a position of an X-ray focus on an anode of an X-ray source of an X-ray imaging system, the regulation device comprising:
   a memory storing computer-executable instructions; and
   at least one processor configured to execute the computer-executable instructions to cause the regulation device to
      determine a combined actual position of the X-ray focus by combining a measured position of the X-ray focus and a model based position of the X-ray focus, the model based position of the X-ray focus determined based on a measurement value of a deflection current,
      generate a manipulated variable based on the combined actual position and a target position, and
      correct a deviation of the position of the X-ray focus from the target position based on the manipulated variable.

* * * * *